United States Patent
Zeng et al.

(10) Patent No.: US 8,185,383 B2
(45) Date of Patent: May 22, 2012

(54) METHODS AND APPARATUS FOR ADAPTING SPEECH CODERS TO IMPROVE COCHLEAR IMPLANT PERFORMANCE

(75) Inventors: Fan-Gang Zeng, Irvine, CA (US); Hongbin Chen, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 1308 days.

(21) Appl. No.: 11/880,240

(22) Filed: Jul. 20, 2007

(65) Prior Publication Data

US 2008/0215332 A1    Sep. 4, 2008

Related U.S. Application Data

(60) Provisional application No. 60/833,076, filed on Jul. 24, 2006.

(51) Int. Cl.
*G10L 11/04* (2006.01)
(52) U.S. Cl. ........................ 704/207
(58) Field of Classification Search ........... 704/207
See application file for complete search history.

(56) References Cited

U.S. PATENT DOCUMENTS

| | | | |
|---|---|---|---|
| 4,532,930 A * | 8/1985 | Crosby et al. | 607/57 |
| 6,889,186 B1 * | 5/2005 | Michaelis | 704/225 |
| 2004/0172101 A1 * | 9/2004 | Van Hoesel | 607/57 |
| 2005/0192646 A1 * | 9/2005 | Grayden et al. | 607/57 |
| 2006/0080087 A1 * | 4/2006 | Vandali et al. | 704/207 |
| 2006/0212095 A1 * | 9/2006 | Wolfe et al. | 607/57 |

OTHER PUBLICATIONS

Green et al, Enhancing temporal cues to voice pitch in continuous interleaved sampling cochlear implant, 2004, Department of Phonetics and Linguistics, pp. 2298-2310.*
Nie et al., Encoding Frequency Modulation to Improve Cochlear Implant Performance in Noise Jan. 2005, IEEE, vol. 52, pp. 64-73.*
Geurts et al., Coding of the fundamental frequency in continuous interleaved sampling processors for cochlear implants Feb. 2001, Acoustical Society of America, pp. 713-726.*
Blake et al., Design and evaluation of continuous interleaved sampling (CIS) processing strategy for multichannel cochlear implants 1993, Journal of Rehabilitation Research and Development, vol. 30 No. 1, pp. 110-116.*
Fan-Gang Zeng, Temporal pitch in electric hearing 2002, Department of Otolaryngology, pp. 101-106.*

* cited by examiner

*Primary Examiner* — Jakieda Jackson
(74) *Attorney, Agent, or Firm* — Dickstein Shapiro LLP

(57) ABSTRACT

Cochlear implant performance is improved by extracting pitch information and encoding such pitch information into the processor of a cochlear implant. One embodiment of the invention is to explicitly extract the pitch and deliver it to the cochlear implant by co-varying the stimulated site and rate. Another embodiment of the invention is to implicitly encode the pitch information via a code book that serves as the carrier of stimulation in the cochlear implant.

21 Claims, 9 Drawing Sheets

METHODS AND APPARATUS FOR ADAPTING SPEECH CODERS TO IMPROVE COCHLEAR IMPLANT PERFORMANCE

CROSS-REFERENCE TO RELATED APPLICATION

This application claims the benefit of U.S. Provisional Application No. 60/833,076, filed Jul. 24, 2006.

STATEMENT REGARDING GOVERNMENT SUPPORT

This invention was made with Government support under NIH/NIDCD, Grant No. R01-DC-02267-07. The Government has certain rights in this invention.

FIELD OF THE INVENTION

The present invention relates generally to speech processing strategies, and more particularly to adapting speech coders to improve the performance of cochlear implants.

BACKGROUND OF THE INVENTION

When the development of speech processing strategies in cochlear implants is compared to that of speech coding algorithms in modern communication, it is apparent that, except for specific earlier versions which used a feature extraction strategy, all current cochlear implants are based on the "channel vocoder" concept. This concept was first conceived and implemented by Horner Dudley at Bell Labs (Dudley 1939). The "channel vocoder" concept, as illustrated in FIG. 1, involves an initial extraction of band-specific temporal envelopes followed by extraction of voice pitch (if the sound was voiced). The extracted band-specific temporal envelopes are then used to amplitude modulate either a periodic pulse train that corresponds to the voice pitch (if the sound was voiced) or a noise (if the sound was unvoiced). Unfortunately, speech synthesized using this channel vocoder concept may be intelligible but may also have a "machine-like" sound quality due to inaccuracy in pitch extraction and/or other factors.

Until recently, the temporal envelope has been thought to be the major cue contributing to speech intelligibility, while fine structure has been thought to contribute mostly to sound quality and speaker identification. However, it now appears that fine structure is crucial to speech recognition in noise, particularly when noise is another competing voice. As such, encoding temporal fine structure in cochlear implants remains a significant challenge. The problem is that while continuous-interleaved-stimulation (CIS) strategies may improve the temporal envelope representation, they all but totally discard the temporal fine structure. Additionally, recently-proposed strategies using higher filter density at low frequencies than at high frequencies to improve fundamental frequency (F0) encoding have the unfortunate drawback of reduced filter density at high frequencies which degrades speech intelligibility. Therefore, methods and apparatus for adapting speech coders to improve cochlear implant performance are needed.

SUMMARY OF THE INVENTION

Disclosed and claimed herein are methods and apparatus for improving sound processing by a cochlear implant. In one embodiment, a method includes receiving sound containing a voiced component, extracting pitch information from said sound for the voiced component, and adding the pitch information into a continuous-interleaved-stimulation processor of the cochlear implant.

Other aspects, features, and techniques of the invention will be apparent to one skilled in the relevant art in view of the following description of the exemplary embodiments of the invention.

DETAILED DESCRIPTION OF THE EXEMPLARY EMBODIMENTS

As used herein, the terms "a" or "an" shall mean one or more than one. The term "plurality" shall mean two or more than two. The term "another" is defined as a second or more. The terms "including" and/or "having" are open ended (e.g., comprising). The term "or" as used herein is to be interpreted as inclusive or meaning any one or any combination. Therefore, "A, B or C" means "any of the following: A; B; C; A and B; A and C; B and C; A, B and C". An exception to this definition will occur only when a combination of elements, functions, steps or acts are in some way inherently mutually exclusive. Reference throughout this document to "one embodiment", "certain embodiments", "an embodiment" or similar term means that a particular feature, structure, or characteristic described in connection with the embodiment is included in at least one embodiment of the present invention. Thus, the appearances of such phrases in various places throughout this specification are not necessarily all referring to the same embodiment. Furthermore, the particular features, structures, or characteristics may be combined in any suitable manner on one or more embodiments without limitation.

Rather than explicitly extracting pitch information, one embodiment of the invention is to provide a phase vocoder which extracts a slowly-varying version of frequency modulation around the center frequency of the analysis filter. In certain embodiments, this achieves significantly improved performance in all functional aspects with normal-hearing subjects listening to the simulations. To that end, a phase vocoder may be modified to extract a slowly-varying frequency modulation (FM) component (e.g., <500 Hz), according to one embodiment of the invention. This extracted slowly-varying FM component may then be added to a cochlear implant or other device (e.g., radio, public address system, stereo) that delivers sounds (e.g., music or voice). In certain embodiments, this may have the desired effect of improving performance in noisy speech recognition, speaker identification, tonal language perception, and melody recognition.

Figure 1:
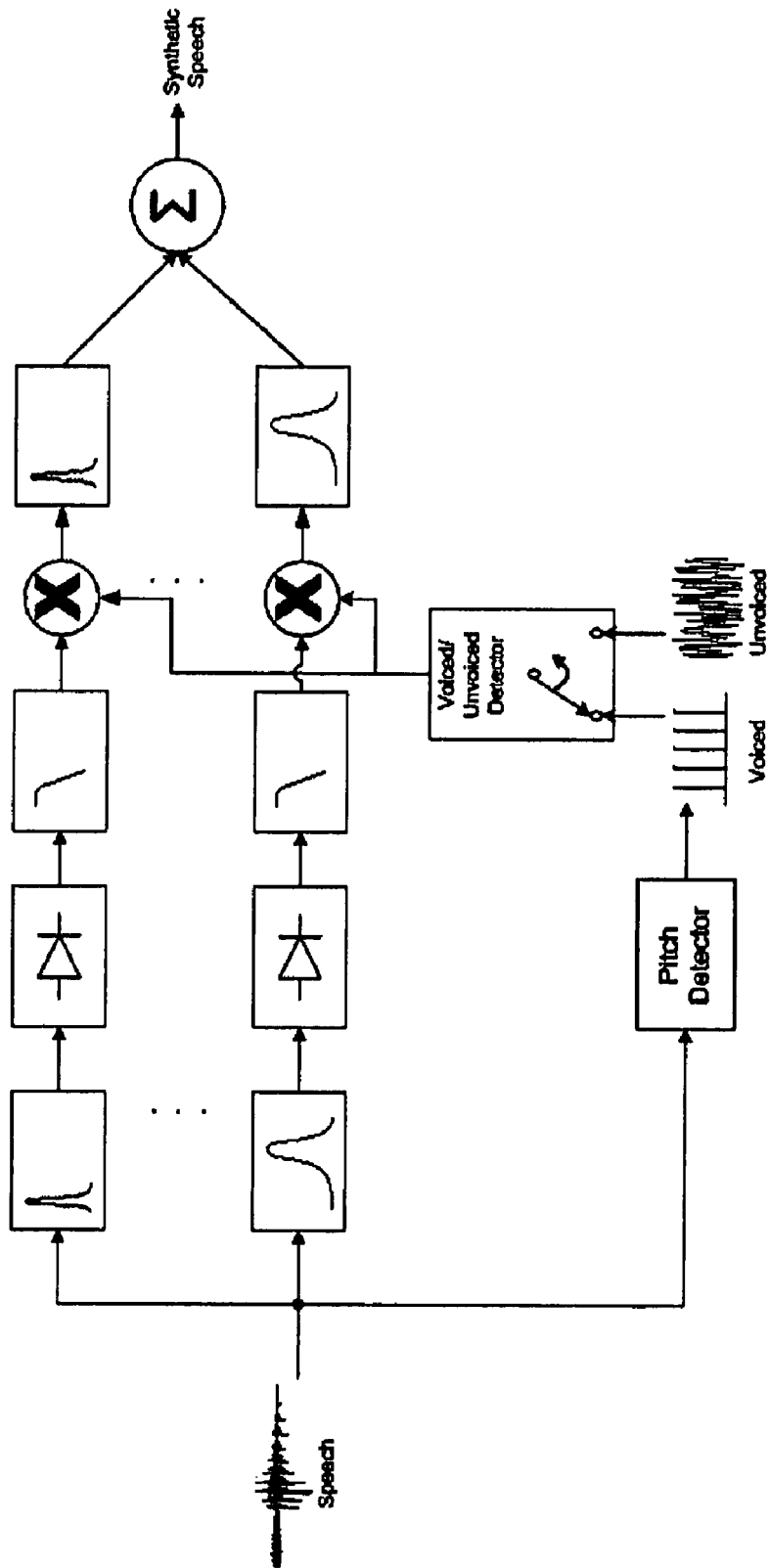
FIG. 1 is a schematic for the channel vocoder implementation of the prior art.
Figure 2:
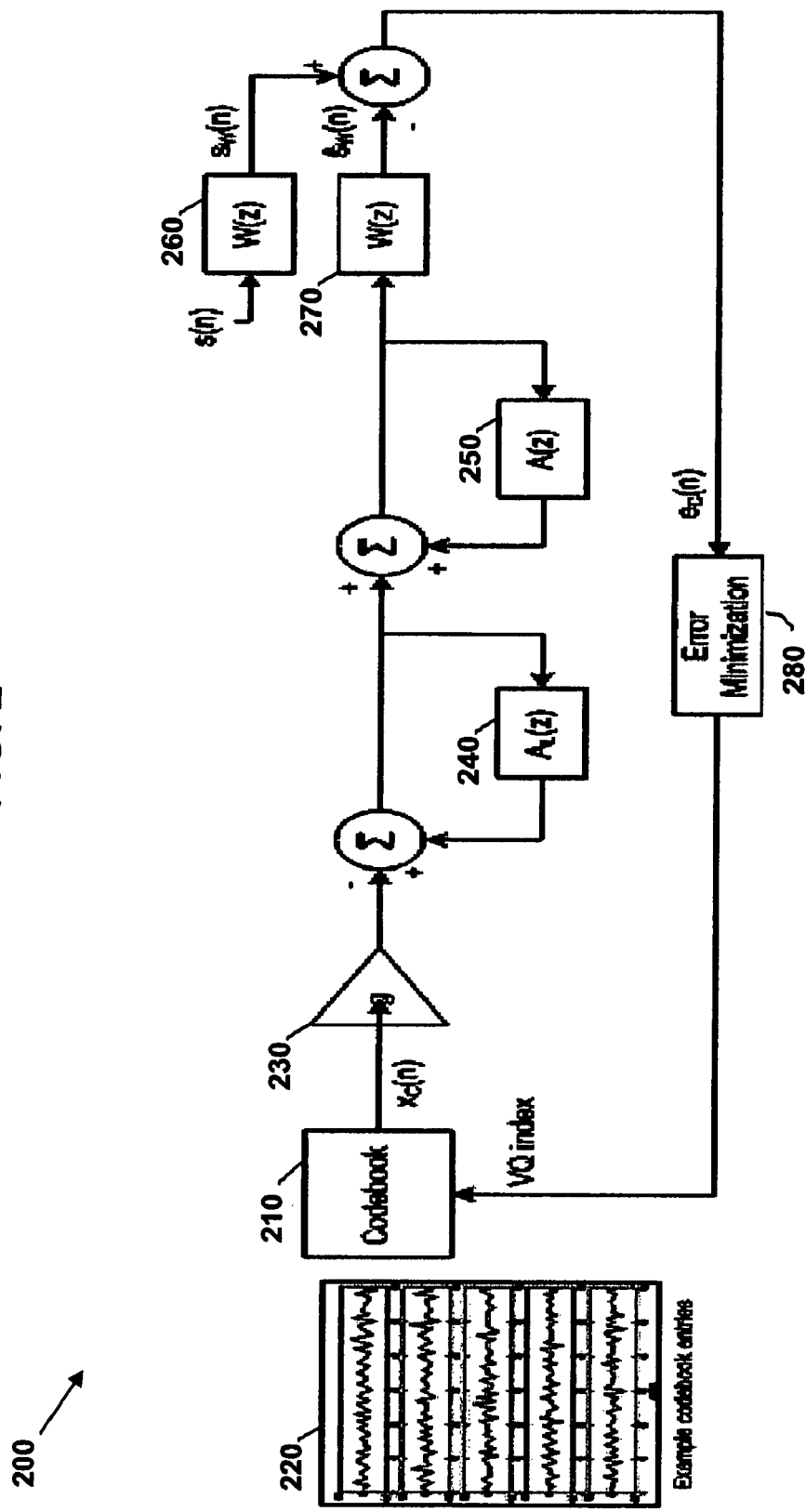
FIG. 2 is a block diagram of a code-excited linear prediction (CELP) vocoder configured in accordance with one embodiment of the invention.

In certain embodiments, the invention provides improvements and/or modifications and/or new uses/modes of use for multi-pulse and code-excited linear prediction (CELP) vocoders that are widely used in telecommunication applications, such as cellular phones. To the end, FIG. 2. depicts one embodiment of a CELP system 200 to achieve both superior sound quality and high coding efficiency (e.g., 4.8-9.6 kbps). As shown, the system 200 includes a codebook 210 to encode fine structure, wherein the codebook 210 includes a plurality of codebook entries 220 corresponding to Gaussian sequences which may be pseudo-periodic or random. In multi-pulse linear predictive coding (LPC), the code entries 220 may include multiple, non-uniformly-spaced pulses.

An entry from the codebook 210 may randomly be selected (x) and scaled up or down via a linear amplifier 230. This scaled entry may then be filtered sequentially through two recursive filters—one with a long-delay predictor 240 for introducing the voice periodicity, and the other with a short-delay predictor 250 for the spectral envelope. The algorithm may use closed-loop optimization by minimizing the error 280 in the perceptually-weighted differences 260 and 270 between the input signal (s) and the coded signal (x).

In one embodiment, the codebook 210 may be adapted to match the implant users' perceptual capability. To that end, the adapted code book 210 may contain temporal templates of pulse trains with various inter-pulse intervals. Implant users are sensitive to these random temporal patterns, and speech recognition may be highly correlated to the ability to discriminate these patterns.

It should further be appreciated that adapting the speech-coding algorithms to cochlear implants may also reduce the development cost since these modified algorithms can be implemented in relatively inexpensive digital signal processor (DSP) chips. Moreover, the code book 210 may be stored inside the internal part of a cochlear implant, thereby improving the implant's transcutaneous transmission efficiency.

The CELP coder of system 200 may be selected for adaptation in accordance with the present disclosure due to its high quality, coding efficiency and low cost. For example, a 10-bit codebook can access 1,024 different temporal patterns. Moreover, because CELP uses a long-term predictor with a delay that may or may not be equal to the pitch period, it does not require explicit pitch extraction. In accordance with certain embodiments of the invention, a perceptually-based codebook (e.g., codebook 210 of FIG. 2) may be used that contains distinguishable temporal patterns for cochlear implant users. In one embodiment, this process starts with the current codebook and translates the code into a pulse train and then obtains a confusion matrix among these temporal patterns. A clustering and/or principle component analysis may be used to determine the critical size of the codebook. One possible implementation is to select the temporal pattern in the codebook that is maximally matched to the input and to use it as the carrier in electric stimulation.

In accordance with another aspect of the invention, the codebook can be stored in the implantable part of the cochlear implant, requiring transmission of only the slowly-varying envelope cues and 8-10 bits of information that selects the carrier in the codebook. The adaptation and implementation of the speech coding algorithms will allow next-generation cochlear implants to be designed on the same platform as the cell phones, bridging the technological gap to improve not only implant performance, but also its cost and efficiency.

As previously mentioned, current cochlear implants may be satisfactory for speech recognition in quiet environments, but are seriously limited in performance related to realistic listening such as music perception, speech recognition in noise, and tonal language understanding. Thus, one aspect of the invention is to improve cochlear implant performance under these more realistic listening conditions (e.g., in situations where there is background noise).

One aspect of the invention is based on the recognition that pitch encoding is important not only for sound quality, but also for noisy speech recognition, speaker identification, auditory scene analysis, music appreciation, and tonal language perception. To that end, one embodiment of the invention is a method for improving performance of a cochlear implant by extracting pitch information and encoding such explicit pitch information into the processor of a cochlear implant. The pitch information may be extracted by any suitable technique, such as either time-domain processing (e.g., autocorrelation) or spectral-domain processing (e.g., flattening LPC). Once the pitch information has been extracted, it may be added to a CIS-based processor using any suitable technique. One such suitable technique that may be used to add the pitch information to a CIS-based processor is to a) split the electrode array into an apical part and a basal part, b) use the apical part (e.g., 8 electrodes) to explicitly encode pitch and c) use the basal part (e.g., 12 electrodes) to encode envelope, much like a standard CIS processor.

Figure 3:
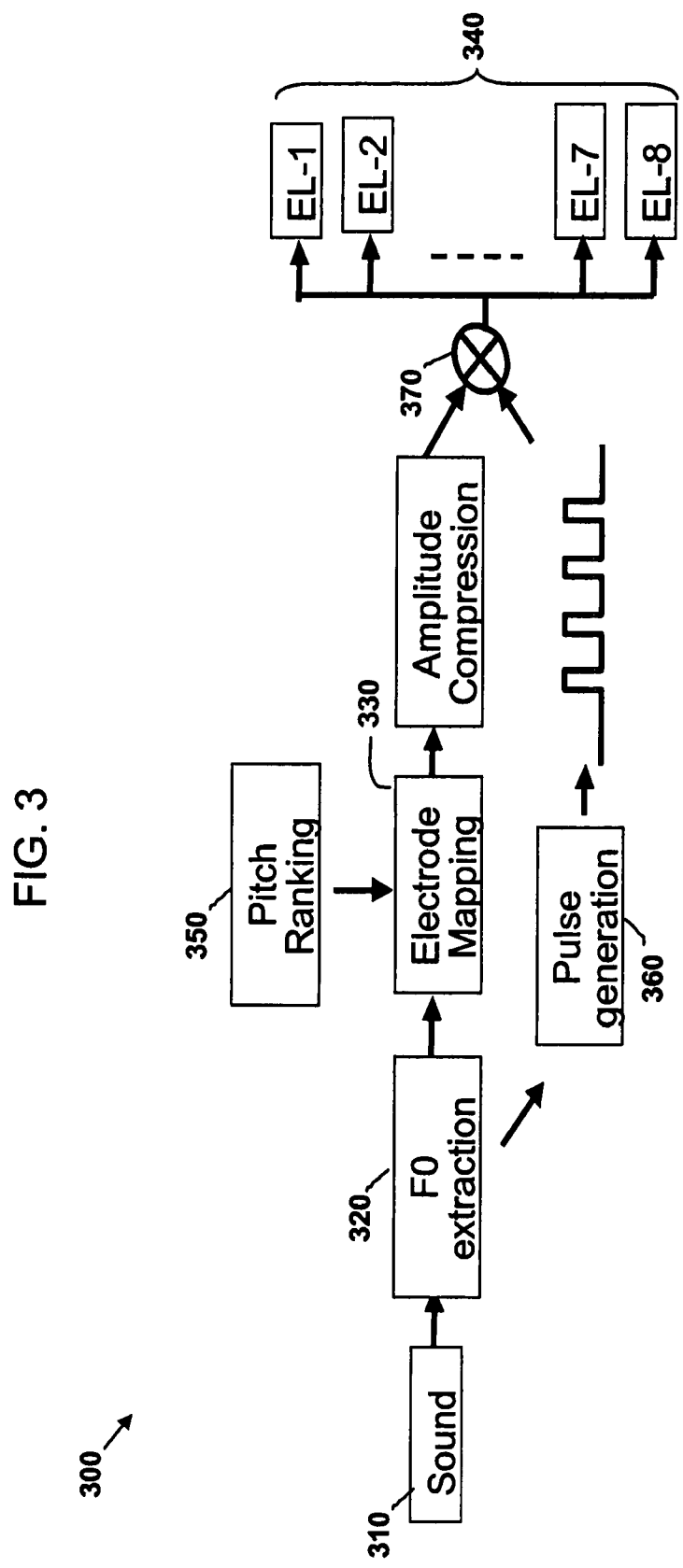
FIG. 3 is a block diagram of a pitch coding algorithm configured in accordance with one embodiment of the invention.

To that end, FIG. 3 depicts one embodiment of a block diagram of a pitch coding algorithm 300 configured to improve cochlear implant performance by extracting pitch information and encoding such explicit pitch information into the implant's processor in accordance with the principles of the invention. As shown, after the sound 310 is received, the fundamental frequency (F0) may be extracted at block 320 and then mapped (block 330) to one of a number (e.g., 8) of apical electrodes 340 according to both rate and place information. The fundamental frequency (F0) relates to the perception of musical pitch or voice pitch, and can be in the range of between about 50 Hz and several hundred Hz. Finer temporal information is provided by the harmonic frequencies of sounds, which may be multiples of F0. As will be described in more detail below, block 350 may be used for pitch ranking based on psychophysical pitch ranking and discrimination data.

Another method for encoding pitch may be to frequency modulate the carrier in a standard CIS processor (block 360). Still another method may be to interleave the electrodes so that the odd-numbered electrodes (e.g., E1, E3, E5*t* . . . and E19) encode pitch whereas the even-numbered electrodes encode the envelope (e.g., E2, E2, E4, . . . and E 20), or vice versa. In one embodiment, this interleaving may be performed at block 370, for example. It should be appreciated that all such may be implemented in real-time using a SPEARS3 processor, for example.

The present invention may be employed to provide significantly improved performance in melody and speaker recognition because of the explicit encoding of pitch in the new strategy, while maintaining state-of-art performance in speech recognition in quiet and in noise because multiple electrodes are still used to encode the temporal envelope information.

In applications where pitch estimation with real-time implementation is problematic, or where adding noise is problematic, computationally intensive algorithms using time-frequency representations may be used to estimate reliably the pitch information.

Figure 4:
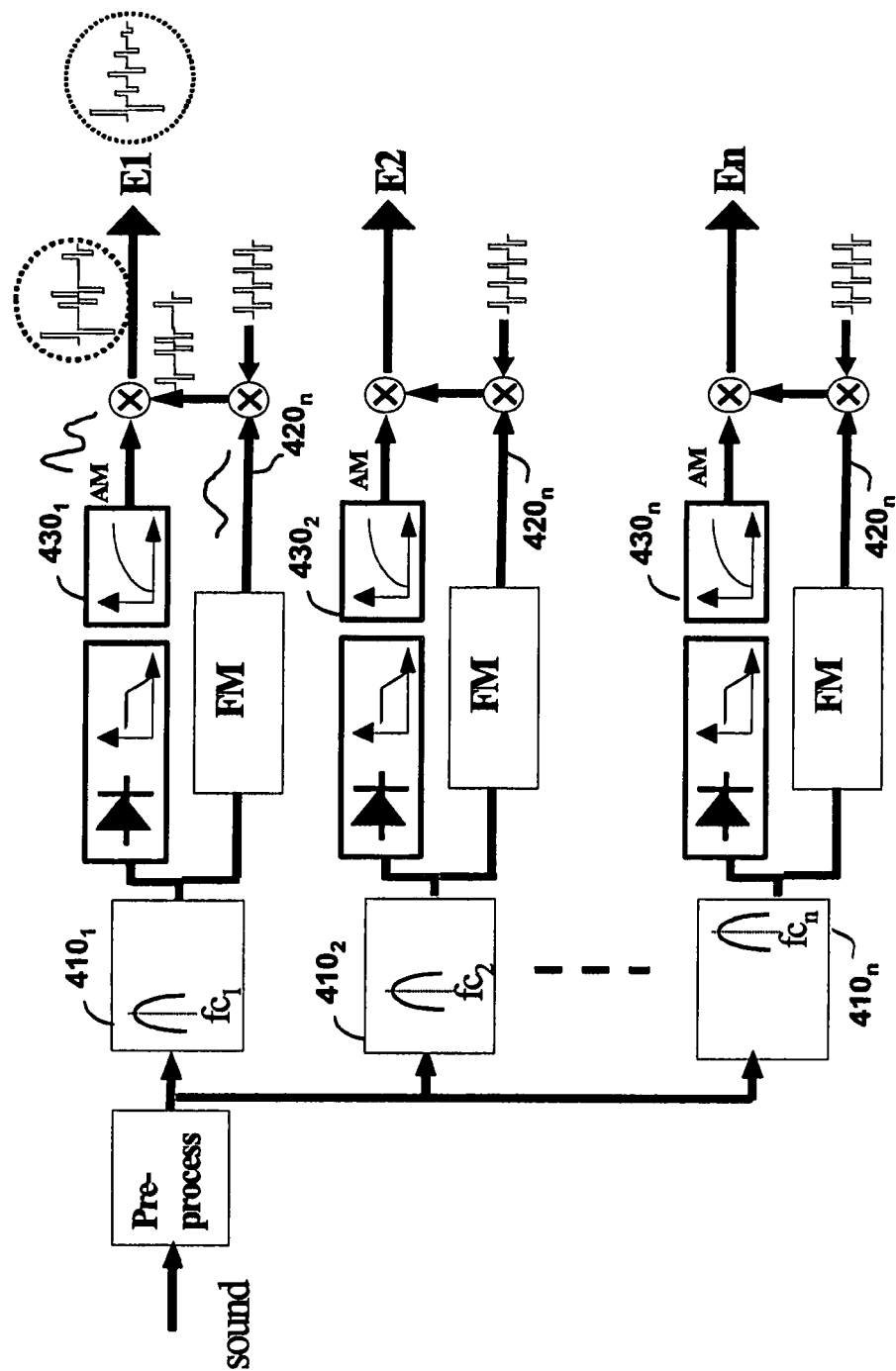
FIG. 4 is one embodiment of a schematic diagram showing one or more approaches for implementing frequency modulation in the current CIS strategy, in accordance with the principles of the invention.

It should be appreciated that the invention may use various methods to implement frequency modulation in the current CIS strategy, an example of which is shown schematically in FIG. 4. In this method, the fixed pulse-rate carrier $410_1$-$410_n$ ("410") is frequency modulated with the slowly-varying FM signal $420_1$-$420_n$ ("420") in the standard CIS strategy. It should be appreciated that this frequency modulation may be in addition to the amplitude modulation $430_1$-$430_n$ ("430") already implemented in the CIS strategy.

In another embodiment, the frequency modulation may be implemented in the current CIS strategy by replacing the fixed pulse-rate carrier 410 entirely with just the slowly-varying FM signal 420. This method may be desirable to save additional battery power since it employs a much slower rate of stimulation than the high-rate stimulation in a typical CIS processor.

Still another embodiment for implementing the frequency modulation in the current CIS strategy may be to employ the N-of-M strategy, in which the frequency modulation signal 420 is implemented at least for the voiced segment of speech, which tends to be more stable and longer than the unvoiced segment.

In devices employing analog-waveform strategies, both amplitude modulation and frequency modulation components may be present, but may not be readily available to the implant user. This is because the amplitude modulation and frequency modulation cues in the sub-band signals are still convolved. Moreover, the frequency modulation rate in the high-frequency sub-bands is likely to be too fast to be perceivable. Thus, a different approach may be employed in such devices by removing the center frequency of the analog sub-band electric signals. Thus, varying embodiments of the invention may be implemented in all current cochlear implant types.

In certain embodiments, frequency modulation detection may be further improved by high-rate carriers/conditioners. To that end, a speech processing strategy may be used to encode both amplitude and frequency modulations so to improve the overall cochlear implant performance.

While one aspect of the invention is to combine pitch encoding and CIS strategy to achieve improved performance for both music and speech, another aspect is to combine rate and place codes to improve pitch. To that end, in one embodiment the stimulation rate and position may be co-varied to encode pitch since neither cochlear place pitch nor temporal pitch is appropriately encoded in current cochlear implants. In one embodiment, a high-rate (5-10 kHz) carriers or "conditioners" may be used to further improve temporal pitch perception, particularly in the middle frequency range (0.5-1.5 kHz), which is not typically accessible by either the stimulation rate or the stimulation place in current implants. High-rate (e.g., >2 kHz, such as between 5-10 kHz)) stimulation restores stochastic properties in auditory nerve responses. To that end, high-rate carriers (as opposed to high-rate conditioners) above about 2 kHz may be used to increase the electric dynamic range and improve rate discrimination and speech recognition. Thus, a high-rate carrier (5-10 kHz) may be used to improve modulation detection and pitch discrimination. This may have the desired benefit of improved pitch perception in the middle frequency range (500-1,500 Hz), which is not adequately encoded by either stimulation rate or electrode position in current implants.

In another embodiment, the place-based pitch perception may be improved using a psychophysically-measured frequency-to-electrode map that conforms to both ranking and ratio scales in the perceived pitch. While all current implant fitting systems have amplitude mapping, none of them has explicit frequency-to-electrode mapping. To that end, in one embodiment, the frequency-to-electrode map not only maintains a monotonic electrode-to-pitch function but also should reflect the interval and/or ratio scale in the original frequency-to-pitch perception, namely, the Mel scale.

In certain embodiments, electrode ranking of the place pitch may resolve the pitch reversal problem, if any, and improve pitch perception with better pitch contour cues. The fully-fledged electrode-pitch function should restore the Mel scale in implant subjects and improve the overall performance in melody and voice pitch recognition.

Figure 5:
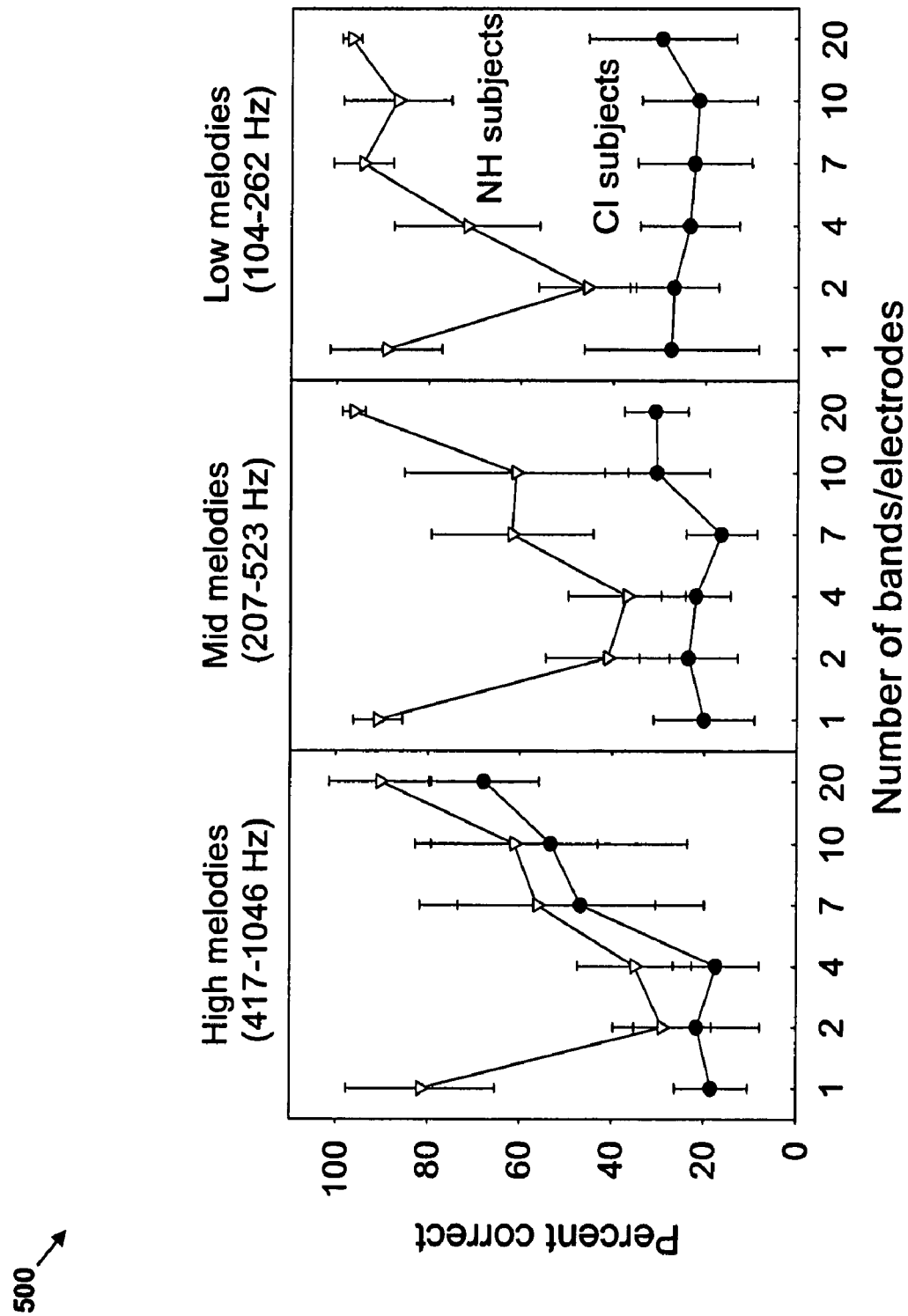
FIG. 5 depicts a graph of melody recognition data illustrating the functional pitch deficit in current implant users.

Referring to FIG. 5, the functional pitch deficit in current implant users is depicted. That is, graph 500 shows melody recognition data collected over 3 frequency ranges (high: 417-1046 Hz, mid: 207-523 Hz, and low: 104-262 Hz) as a function of the number of bands/electrodes in normal subjects listening to implant simulations (plotted as triangles), and for implant subjects (plotted as filled circles). As shown, normal-hearing subjects were able to use both place (improved performance with increasing number of bands in all melody conditions) and temporal cues (as evidenced by the high level of performance with the 1-band condition). The implant subjects could only use place information in the high-range melody condition (see gradually increased performance with the number of electrodes) but received no temporal information at all (essentially chance level performance independent of the number of electrodes in the low and middle melodies). With that, another aspect of the invention is to use a high-rate carrier (not a high-rate conditioner) to improve temporal pitch perception. For example, the pulse rate or the modulation frequency of a half-wave rectified, sinusoidally-amplitude-modulated (SAM) 5-kHz pulse train may be modified. In certain embodiments, the difference limen was significantly smaller for SAM modulation frequencies at high rates, e.g., >2 kHz.

Figure 6:
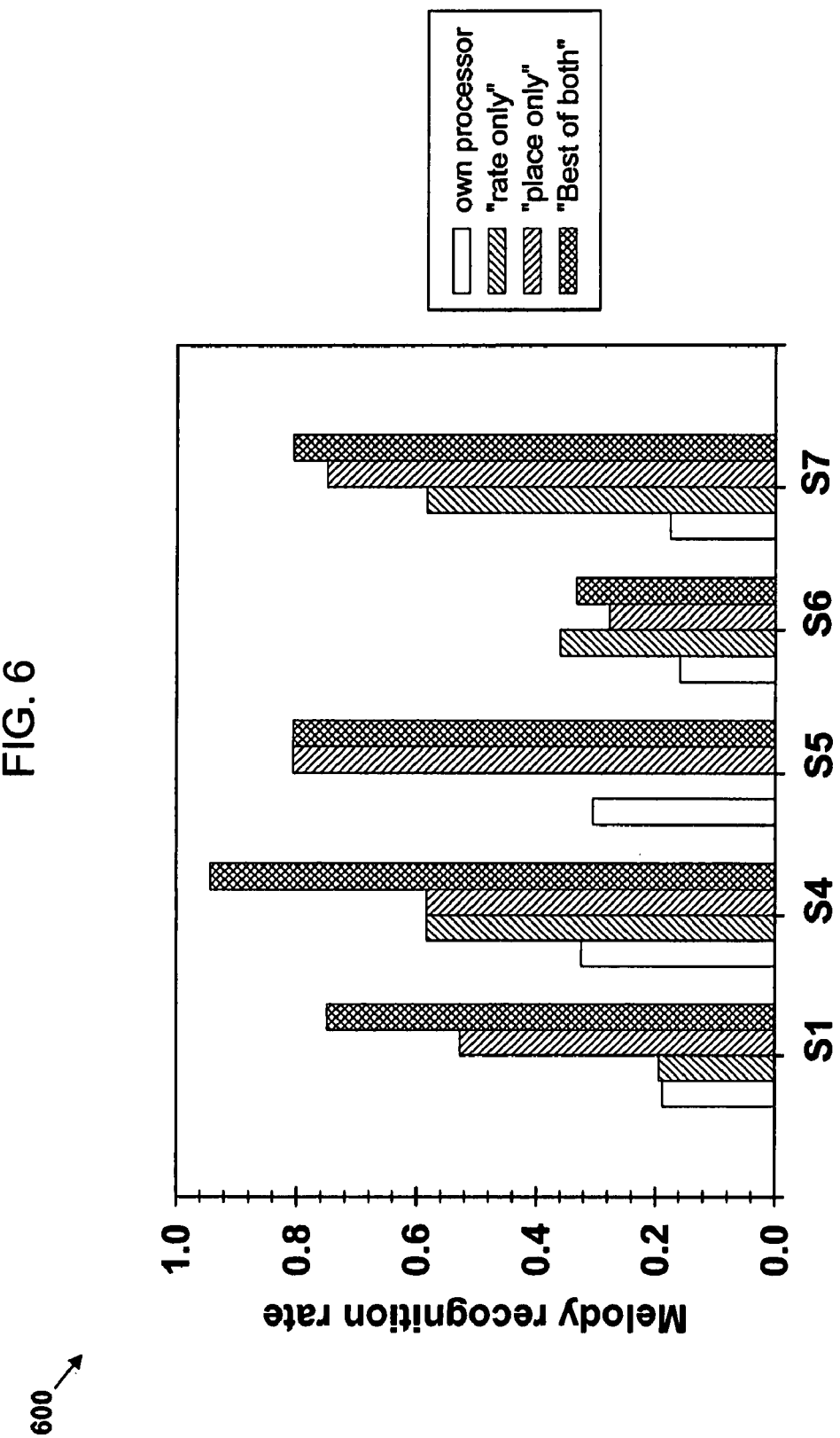
FIG. 6 depicts a graphical representation of melody recognition may be improved for cochlear patients by encoding the melody using the stimulation rate, the electrode position, and a combination of the two, according to one embodiment of the invention.

Referring now to FIG. 6, depicted is data showing melody recognition for cochlear patients wherein the melody has been encoded using the stimulation rate, the electrode position, as well as a combination of the two. In particular, graph 600 depicts melody recognition information for 5 random subjects, Si, S4, S5, S6 and S7. The melody recognition resulting from using only the stimulation rate to encode melody is being shown by the left-slanted hatched bars of graph 600. The same measurement may then be performed using only the electrode position to encode the melody (e.g., a constant rate of 100 Hz, 1000 Hz, etc.), as shown by the right-slanted hatched bars of graph 600. Finally, the combined rate and the electrode position may be used to encode melody (shown by the crossed-hatched bars of graph 600). In the combined condition, a musical note may be encoded by different stimulation rates on the same electrode or the same stimulation rate on different electrodes depending on its frequency.

Pitch information may be delivered to cochlear implant users based on the optimal performance obtained with rate pitch and place pitch. Table 1 below shows an example on how a combined rate and place pitch map may be constructed to encode the 132-526 Hz pitch range used in graph 600 of FIG. 6:

TABLE 1

Rate only, place only and combined rate and place pitch

| Map | Electrode # (stimulation rate) | Pitch range encoded | Spectral resolution |
|---|---|---|---|
| Rate only | #20 (132-526 Hz) | 132-526 Hz | ~2 octaves/electrode |
| Place only | #20 (1000 Hz) | 132-186 Hz | ~0.5 octave/electrode |
|  | #19 (1000 Hz) | 187-262 |  |
|  | #18 (1000 Hz) | 263-372 |  |
|  | #17 (1000 Hz) | 372-526 |  |
| Combined | #20 (132-186 Hz) | 132-186 Hz | ~0.5 octave/electrode |
|  | #19 (187-262 Hz) | 187-262 |  |
|  | #18 (263-372 Hz) | 263-372 |  |
|  | #17 (372-526 Hz) | 372-526 |  |

The "rate only" map of Table 1 uses 1 electrode (e.g., BP+1), but varies the stimulation rate to encode the entire pitch range. The "place only" map of Table 1 uses multiple electrodes (4 in this case) but fixed stimulation rate to encode the pitch. Finally, the "combined" map of Table 1 uses both the place and rate of stimulation to encode the pitch. It should be appreciated that the exact number of electrodes, the place of the electrode, and the range of stimulation rate may be derived from individually measured psychophysical data.

If an individual can discriminate among all electrodes, then the number of electrodes may be increased (e.g., to 8) so as to improve the spectral representation of F0 while having sufficient number of electrodes available for programming a standard CIS processor. If, on the other hand, an individual cannot discriminate between electrodes (e.g., #20 and #19), then one of them may be omitted. On the other hand, if one electrode (e.g., #20) produced a higher pitch percept than another electrode (e.g., #19)(i.e., pitch reversal), then they may be switched. Similarly, the range of stimulation rate on each electrode can be adjusted to reflect the individual subject's sensitivity to rate changes. In certain embodiments, depending on frequency, electric pitch can be represented by different stimulation rates on different electrodes.

Figure 7:
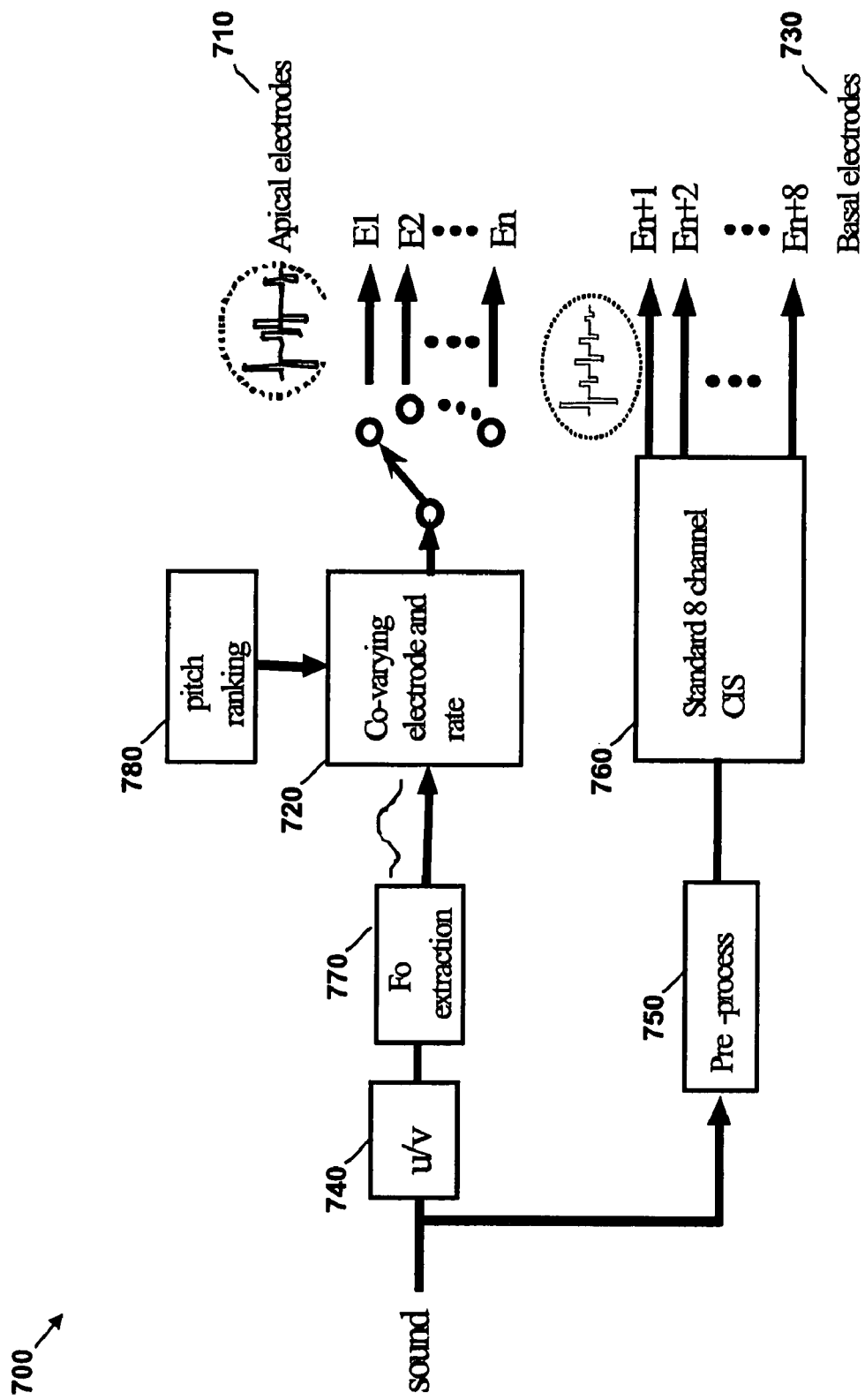
FIG. 7 depicts another embodiment of a functional diagram of an encoding strategy in accordance with the principles of the invention.

FIG. 7 depicts another embodiment of a functional diagram of a "CIS+F0" strategy in accordance with the principles of the invention, which incorporates both place-coding of F0 by relatively narrow-filters and temporal-coding of F0 by dynamically varying the stimulation rate. As shown, diagram 700 uses apical electrodes 710 to explicitly encode F0 by co-varying the stimulation place and the stimulation rate at block 720. In addition, basal electrodes 730 may be used to perform a standard 8-channel CIS processing.

In the depicted "CIS+F0" strategy of FIG. 7, a determination is first made as to whether an incoming sound is unvoiced or voiced at block 740. If the sound is unvoiced, then no F0 is extracted and no apical electrodes are stimulated. The unvoiced sound may be pre-processed at block 750 and then processed in accordance with the standard CIS at block 760.

If, on the other hand, the sound is determined at block 740 to be voiced then the F0 may be extracted at block 770 using, for example, an auto-correlation method with a center-clipped input. In certain embodiments, the F0 determines which electrode is stimulated and at what rate, based on psychophysical pitch ranking and discrimination data from block 780. Table 1 above shows an example how the F0 may be encoded by co-varying both the stimulation rate and the stimulation place.

Spectral Contrast Enhancement

In certain embodiments, strategically enhancing spectral contrast may be used to improve neural speech representation and cochlear implant performance. To that end, a companding strategy may be implemented to produce spectral enhancement by setting one or more of three companding parameters. First, the companding ratio (n1/n2), which controls the degree of spectral contrast enhancement, may be set to 0.3 in one embodiment, but may also be varied at 0.1, 0.3, 0.6, and 1. The second parameter is the quality factor (Q) of the pre- and post-compression filters which controls the locality of spectral contrast enhancement. In one embodiment, a ratio of approximately 2:12 may be used, although ratios of 2:4, 2:6, 2:12, 4:6, 4:8 and 4:12 may also be used in other embodiments. The third parameter is the number of filters used, which may vary from 8, 16, 32, and 64 so as to roughly reflect the number of electrodes available in current and future cochlear implants.

In another embodiment, companding performance may be further optimized by replacing the symmetrical filters in current companding implementations with asymmetrical filters. In a normal ear, the auditory filter shape is not symmetrical, but has a much shallower slope on the low-frequency side than the high-frequency side. Thus, asymmetrical filters may be used in the pre-compression filter bank in order to mimic the normal cochlear filter function. The low-frequency side slope may be reduced by a factor of 2, 4, and 8.

Additionally, companding performance may be further optimized by performing companding only in the steady-state portion of speech sounds (e.g., vowels or fricatives) with the initial 20-ms duration of a speech segment being unprocessed.

In certain embodiments, the real-time or even online implementation of the companding strategy described herein may require more than 50 filters before and after compression. Thus, an analog version of the companding strategy may be used as a front-end to the cochlear implant speech processor. Alternatively, a lateral inhibition neural network, which produces similar spectral enhancement in the auditory and visual systems, may be more easily implemented in real time than the companding strategy.

Temporal Contrast Enhancement

A significant correlation has been observed between speech recognition and temporal modulation detection, particularly when the modulation detection was measured as a function of stimulus level. A so-called transient emphasis spectral maxima (TESM) is known to improve soft consonant recognition in noise. While TESM indeed enhanced the short duration cues accompanying nasal and stop consonants, it was detrimental to fricative recognition due to excessive amplification of the fricative burst. One problem with the TESM strategy is that the transient gain is only dependent on the onset slope of the acoustic signal within the same frequency channel. Other important acoustic parameters are ignored, including the stimulus level, offset slope, and cross-channel level differences.

Thus, another aspect of the invention is to modify the TESM strategy to adaptively change the transient gain as a function of the stimulus level. Maximal gain may be applied when the stimulus level is low (i.e., at or near threshold) but no gain need be applied when the stimulus level is high (i.e., near maximal comfortable level). In one embodiment, equation (1) below may be used to adaptively control the transient gain:

$$y = (A + Bx)^n + C, \tag{1}$$

where x=the input signal level, which will be used to adaptively modify the transient gain $G' = G \times y$ so that $G' \approx G$ (i.e. gain is unchanged compared with the standard TESM strategy) for low signal levels but reduced for higher levels.

Figure 8:
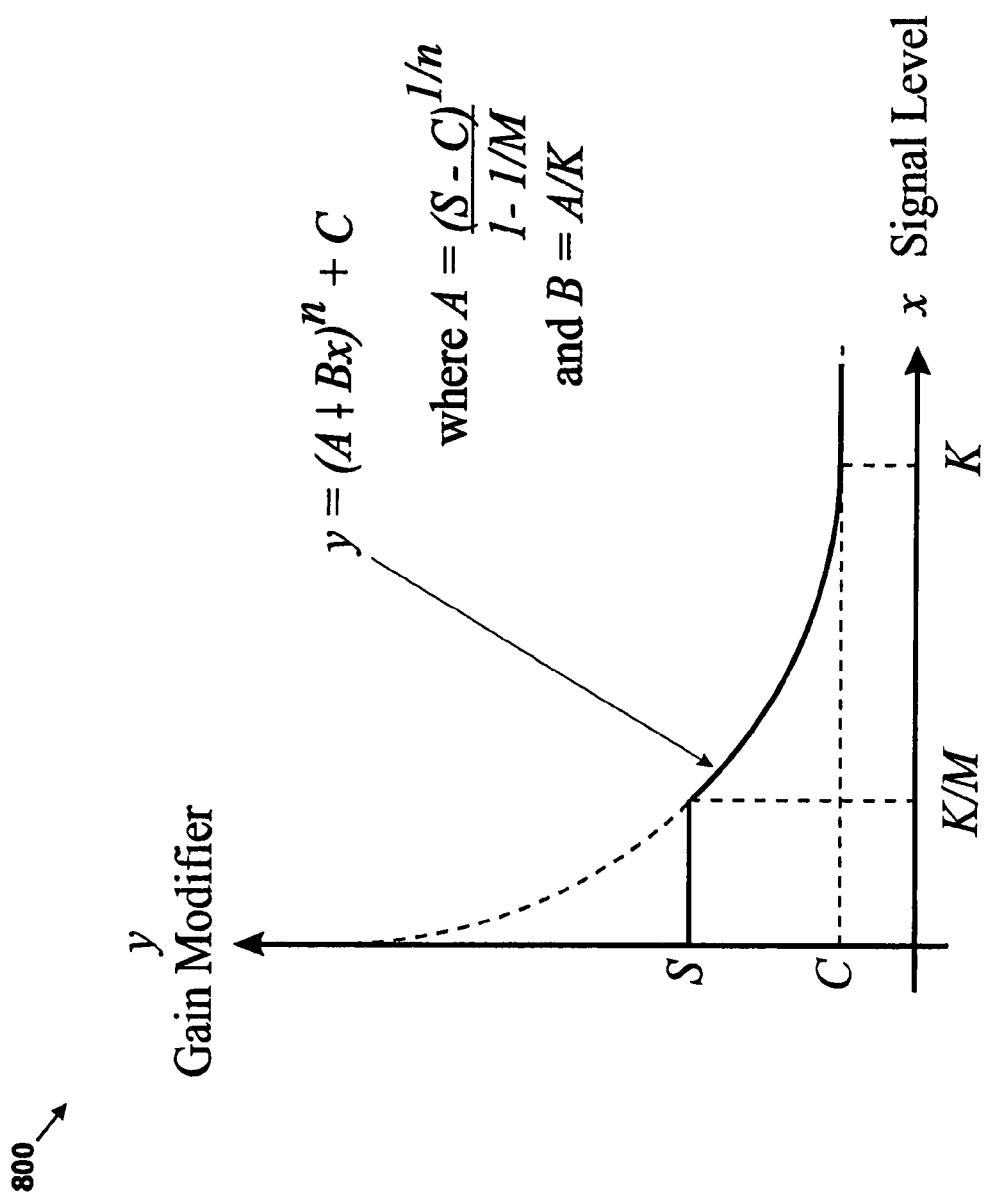
FIG. 8 is a graph showing how the transient gain may be monotonically reduced as a function of the input signal level, according to one embodiment of the invention.

Referring now to FIG. 8, depicted is one embodiment of a graph 800 showing how the transient gain may be monotonically reduced as a function of the input signal level. Assuming a usable signal dynamic range within each channel of about 40 dB, M may be set equal to 100 and K equal to the channel level at which C-level occurs. A maximum gain may be provided for signal levels near threshold but no gain for signals 40 dB above threshold. The parameter n may be used to control the steepness of the function and can be used to match the function to the individual temporal masking data.

In another embodiment, the transient gain rule may also be modified as a function of time to account for reduced overshoot at the stimulus offset. To that end, equation (2) below may be used:

$$G = \frac{2*E_c - E_p - E_f}{E_c + E_p + E_f}, \quad (2)$$

where $E_c$, $E_p$, and $E_f$ represent the signal envelope level in the current, past, and future frame, respectively.

It should be noted that the numerator in equation (2) has been modified to the present form so as to reduce the effect of past envelope energy. In doing this, both onset and offset transients would produce similar amounts of gain.

In still another embodiment, the transient gain rule may be modified to account for the cross-channel temporal masking effect. Essentially, the same rule as in the time domain above can be applied to the transient gain control in the spectral domain:

$$G = \frac{2*E_m - E_l - E_h}{E_m + E_l + E_h}, \quad (3)$$

where $E_m$, $E_l$, and $E_h$ represent the signal envelope level in the middle, lower, and higher frequency channels, respectively.

The proposed modifications of the transient gain in level, time, and frequency (across channels) may function to restore normal temporal masking patterns in cochlear implant users, which may improve both speech intelligibility and listening comfort. Specifically, the modified TESM strategy described above may improve consonant recognition more than vowel recognition due to the improved representation of transient acoustic cues. In addition, the modified strategy may also serve to improve listening comfort because the adaptive gain control will not likely produce large abrupt changes in loudness at high sensation levels.

Figure 9:
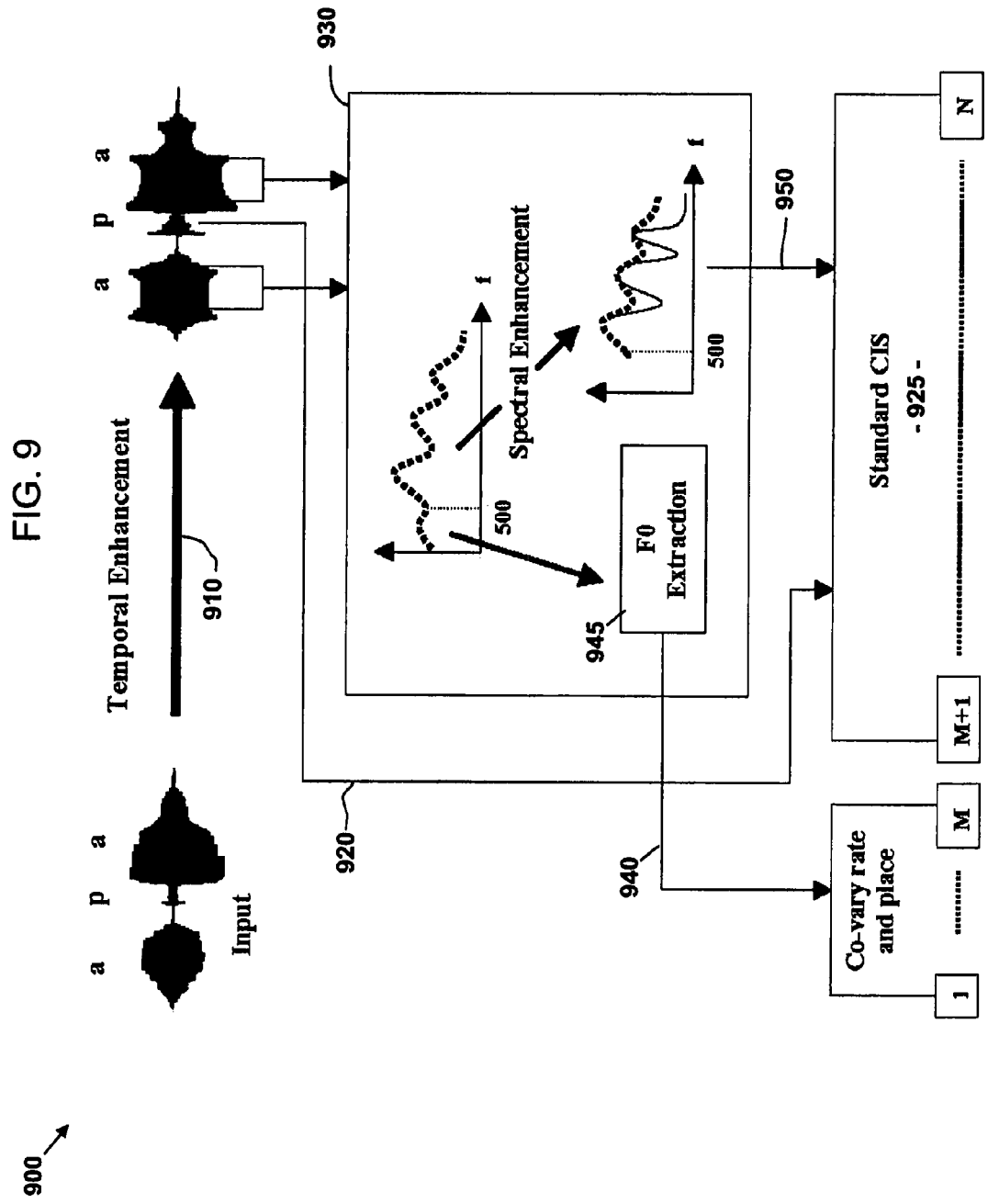
FIG. 9 depicts a block diagram of one embodiment of a combinatory strategy for improving cochlear implant performance.

FIG. 9 depicts a diagram of one embodiment of a combinatory strategy 900 for improving cochlear implant performance. As shown, the input sound may go through the modified TESM strategy 910 described above in order to enhance transients, onsets, and offsets. The enhanced transients, onsets and offsets 920 may then be provided to the standard CIS strategy 925, while the steady-state portion of the signal may then be subject to companding in order to enhance spectral contrast at block 930. Finally, the temporally- and spectrally-enhanced signal may be divided into a low-frequency part 940 and high-frequency part 950, where the division can be set at 500 Hz, for example, or lower or higher depending on individual capabilities. The low-frequency part 940 may then be used to extract pitch, in accordance with the principles described above, at block 945. This extracted pitch may then be used to stimulate one of the apical electrodes (1–m) at the F0 rate. The high-frequency part 950, on the other hand, may be used to stimulate the remaining basal electrodes (m+1–N) using either the standard CIS strategy 925 or the FAME strategy.

In this fashion, the proposed techniques will enhance F0, spectral contrast, and temporal contrast, which, in turn, will improve voice pitch, vowel, and consonant recognition, respectively.

It should be appreciated that algorithms implementing certain aspects of the invention may be used in both current and future cochlear implants by downloading them to the implants' speech processors. Moreover, simplified versions of the coding algorithms may be used to improve current speech coders' efficiency, particularly when the transmitted voice is of music, tonal languages, and mixture of several voices.

A primary use of the disclosed invention is to improve cochlear implant performance in realistic listening conditions. Other uses of the disclosed invention include but are not limited to the improvement of telecommunication transmission efficiency and improvement of the quality of music and speech sounds.

While the invention has been described in connection with various embodiments, it should be understood that the invention is capable of further modifications. This application is intended to cover any variations, uses or adaptation of the invention following, in general, the principles of the invention, and including such departures from the present disclosure as come within the known and customary practice within the art to which the invention pertains.

What is claimed is:

1. A method for improving sound processing by a cochlear implant comprising the acts of:
   receiving sound containing a voiced component;
   extracting pitch information from said sound for the voiced component; and
   adding said pitch information into a continuous-interleaved-stimulation (CIS) processor of the cochlear implant, wherein a stimulation rate and position is covaried to encode the pitch information.

2. The method of claim 1, wherein extracting pitch information comprises extracting pitch information using one of time-domain processing and spectral-domain processing.

3. The method of claim 1, further comprising extracting a slowly-varying frequency modulation (FM) signal from said sound.

4. The method of claim 3, wherein extracting the slow-varying FM signal comprises extracting the slow-varying FM signal using a phase vocoder, and wherein the slow-varying FM signal is extracted around a center frequency of an analysis filter of the phase vocoder.

5. The method of claim 3, further comprising adding the slow-varying FM signal into the CIS processor.

6. The method of claim 3, further comprising adapting a code-excited linear predictive (CELP) vocoder using the slow-varying FM signal.

7. The method of claim 6, wherein the CELP vocoder comprises a codebook containing distinguishable temporal patterns, and wherein said code book is available to the CIS processor.

8. The method of claim 7, further comprising storing the codebook in an implantable part of the cochlear implant.

9. The method of claim 1, wherein adding the pitch information comprises mapping the pitch information to a set of basal electrodes of the cochlear implant.

10. The method of claim 9, further comprising mapping temporal envelopes to a set of apical electrodes of the cochlear implant.

11. The method of claim 1, further comprising frequency modulating a carrier of the CIS processor.

12. A cochlear implant comprising:
a receiver configured to receive sound containing a voiced component;
an extraction module configured to extract pitch information from said sound for the voiced component; and
an encoding module configured to add said pitch information into a continuous-interleaved-stimulation (CIS) processor of the cochlear implant, wherein a stimulation rate and position is covaried to encode the pitch information.

13. The cochlear implant of claim 12, wherein the extraction module uses one of time-domain processing and spectral-domain processing.

14. The cochlear implant of claim 12, wherein the extraction module is further configured to extract a slowly-varying frequency modulation (FM) signal from said sound.

15. The cochlear implant of claim 14, wherein extraction module comprises a phase vocoder to extract the slow-varying FM signal, and wherein the slow-varying FM signal is extracted around a center frequency of an analysis filter of the phase vocoder.

16. The cochlear implant of claim 14, wherein the encoding module is further configured to add the slow-varying FM signal into the CIS processor.

17. The cochlear implant of claim 14, further comprising a code-excited linear predictive (CELP) vocoder configured to use the slow-varying FM signal.

18. The cochlear implant of claim 17, wherein the CELP vocoder comprises a codebook containing distinguishable temporal patterns, and wherein said code book is available to the CIS processor.

19. The cochlear implant of claim 18, wherein the codebook in is stored in an implantable part of the cochlear implant.

20. The cochlear implant of claim 14, wherein the encoding module is configured to map the pitch information to a set of basal electrodes of the cochlear implant.

21. The cochlear implant of claim 20, wherein the encoding module is further configured to map temporal envelopes to a set of apical electrodes of the cochlear implant.

* * * * *